US006865421B2

(12) United States Patent
Bradley

(10) Patent No.: US 6,865,421 B2
(45) Date of Patent: Mar. 8, 2005

(54) METHOD AND APPARATUS FOR AUTOMATIC CAPTURE VERIFICATION USING POLARITY DISCRIMINATION OF EVOKED RESPONSE

(75) Inventor: Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 461 days.

(21) Appl. No.: 10/068,835

(22) Filed: Feb. 8, 2002

(65) Prior Publication Data

US 2003/0153957 A1 Aug. 14, 2003

(51) Int. Cl.[7] .............................................. A61N 1/365
(52) U.S. Cl. ........................................................ 607/27
(58) Field of Search ........................ 607/9, 11, 27–29; 600/509

(56) References Cited

U.S. PATENT DOCUMENTS 5,861,013 A    1/1999   Peck et al. ..................... 607/28
5,871,512 A *  2/1999   Hemming et al. ............. 607/28
5,954,756 A    9/1999   Hemming et al. ............. 607/28

* cited by examiner

Primary Examiner—George Manuel

(57) ABSTRACT

A cardiac stimulation device and method automatically confirm capture by detecting the polarity of a post-stimulation signal. A capture detection circuit is subjected to recharge and block overlap signals applied such than an evoked response signal is characterized by a primarily positive polarity and a polarization signal is characterized by a primarily negative polarity. An amplitude detection feature, such as peak amplitude or signal integral, and its polarity are determined from a post-stimulation signal sensed by the capture detection circuit during a capture detection window. Capture is confirmed when the amplitude detection feature has a positive polarity.

37 Claims, 8 Drawing Sheets

METHOD AND APPARATUS FOR AUTOMATIC CAPTURE VERIFICATION USING POLARITY DISCRIMINATION OF EVOKED RESPONSE

FIELD OF THE INVENTION

The present invention relates to an implantable cardiac stimulation device capable of automatically verifying capture. More specifically, the present invention relates to a device and method wherein sensing circuitry allows capture detection based on the determination of the polarity of a post-stimulation signal feature.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

"Threshold" is defined as the lowest stimulation pulse energy at which capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. If a loss of capture is detected by such "capture-verification" algorithms, a threshold test is performed by the cardiac pacing device in order to re-determine the threshold and automatically adjust the stimulating pulse energy. This approach, called "automatic capture", improves the cardiac stimulation device performance in at least two ways: 1) by verifying that the stimulation pulse delivered to the patient's heart has been effective, and 2) greatly increasing the device's battery longevity by conserving the battery charge used to generate stimulation pulses.

Commonly implemented techniques for verifying that capture has occurred involve monitoring the internal cardiac electrogram (EGM) signals received on the implanted cardiac electrodes. When a stimulation pulse is delivered to the heart, the EGM signals that are manifest concurrent with depolarization of the myocardium are examined. When capture occurs, an "evoked response" may be detected, which is seen as the intracardiac P-wave or R-wave on the EGM that indicates contraction of the respective cardiac tissue. Through sampling and signal processing algorithms, the presence of an evoked response following a stimulation pulse is determined. For example, if a stimulation pulse is applied to the ventricle, an R-wave sensed by ventricular sensing circuits of the pacemaker immediately following application of the ventricular stimulation pulse evidences capture of the ventricles.

If no evoked response is detected, typically a high-energy back-up stimulation pulse is delivered to the heart within a short period of time in order to prevent asystole. An automatic threshold test is next invoked in order to re-determine the minimum pulse energy required to capture the heart. An exemplary automatic threshold determination procedure is performed by first increasing the stimulation pulse output level to a relatively high predetermined testing level at which capture is certain to occur. Thereafter the output level is progressively decremented until capture is lost. The stimulation pulse energy is then set to a level safely above the lowest output level at which capture was attained. Thus, reliable capture verification is of utmost importance in proper determination of the threshold.

Conventional cardiac stimulation devices include single-chamber or dual-chamber pacemakers or implantable defibrillators. A single-chamber device is used to deliver stimulation to only one heart chamber, typically the right atrium or the right ventricle. A dual-chamber stimulation device is used to stimulate both an atrial and ventricular chamber, for example the right atrium and the right ventricle. It has become apparent in clinical practice that the timing interval between atrial stimulation and ventricular stimulation, known as the AV interval or AV delay, can be important in achieving the desired benefit of dual chamber pacing. Hence, capture verification in each chamber is important in maintaining the desired atrial-ventricular synchrony.

Mounting clinical evidence now supports the evolution of cardiac stimulating devices capable of stimulating both the left and right heart chambers, e.g. the left and right atrium or the left and right ventricle, or even three or all four heart chambers. Therapeutic applications indicated for bi-chamber (left and right heart chamber) stimulation or multi-chamber stimulation include stabilization of arrhythmias or re-synchronization of heart chamber contractions in patients suffering from congestive heart failure. The precise synchronization of the left and right heart chamber depolarizations is expected to be important in achieving the desired hemodynamic or anti-arrhythmic benefit. Thus, verifying capture in each chamber being stimulated would be important in maintaining the desired stimulation benefit.

Sensing an evoked response locally, however, can be difficult because of lead polarization that occurs at the lead-tissue interface whenever a stimulation pulse is delivered. A lead-tissue interface is that point at which an electrode of the pacemaker lead contacts the cardiac tissue. Lead polarization is commonly caused by electrochemical reactions that occur at the lead-tissue interface due to application of an electrical stimulation pulse across the interface. If the evoked response is sensed through the same lead electrodes through which the stimulation pulses are delivered, the resulting polarization signal, also referred to as an "afterpotential," formed at the electrode can corrupt the evoked response signal that is sensed by the sensing circuits. This undesirable situation occurs often because the polarization signal can be three or more orders of magnitude greater than the evoked response signal. Furthermore, the lead polarization signal is not easily characterized; it is a complex function of the lead materials, lead geometry, tissue impedance, stimulation energy and other variables, many of which are continually changing over time.

In each of the above cases, the result may be a false positive detection of an evoked response. Such an error leads to a false capture indication, which in turn leads to missed heartbeats, a highly undesirable and potentially life-threatening situation. Another problem results from a failure by the pacemaker to detect an evoked response that has actually occurred. In that case, a loss of capture is indicated when capture is in fact present, which is also an undesirable situation that will cause the pacemaker to unnecessarily invoke the threshold testing function in a chamber of the heart.

The importance of the problem of lead polarization is evident by the numerous approaches that have been proposed for overcoming this problem. For example, specially designed electrodes with properties that reduce the polarization effect have been proposed.

More stringent signal processing algorithms for analyzing the EGM signal may also be applied in order to detect features that indicate an evoked response is present and distinguish it from a polarization signal. A straight-forward method for analyzing the EGM signal is to set an evoked response sensitivity threshold. If a sensed EGM signal exceeds this evoked response sensitivity threshold within a given timeframe following delivery of the stimulation pulse, capture can be verified. However, the evoked response signal and the polarization signal may be similar in morphology and polarity. Other processing algorithms used to differentiate the evoked response from the polarization signal may include integration of the EGM signal, differentiation of the EGM signal, or template matching of the EGM signal to known depolarization morphologies. However as, processing algorithms become more complicated, additional microprocessing time is required, which is already limited due to the numerous device functions that must be performed, and battery consumption is increased.

Another approach to avoiding the problem of lead polarization is to detect evidence of the actual contraction of the heart chambers by measuring a physiological signal other than the EGM such as blood pressure, blood flow, heart wall motion, or changes in cardiac impedance. The use of additional physiological sensors, however, adds cost, more complicated software and hardware requirements, and increases reliability issues and implant time.

It would therefore be desirable to provide reliable capture verification in a cardiac stimulation device using a method that is relatively straight-forward to implement, and that clearly distinguishes between a locally detected evoked response and the polarization signal without requiring additional sensors or complicated processing algorithms.

SUMMARY OF THE INVENTION

The present invention addresses this need by providing an implantable cardiac stimulation device that has the capability to adjust the processing of the post-pacing sensed signals, such that the capture-detection feature is "phasically placed" to enhance capture verification. More specifically, the stimulation device is capable of performing reliable capture verification using sensing circuitry that allows the evoked response and polarization signals to be distinguished by their polarity.

The foregoing and other features of the present invention are realized by providing an implantable, cardiac stimulation device equipped with sensing circuitry and cardiac data acquisition capabilities that are suitable for the collection and analysis of a post-stimulation cardiac signal for the purpose of verifying capture. A preferred embodiment of the stimulation device includes a control system for controlling the operation of the device; a set of leads possessing electrodes for receiving cardiac signals and for delivering atrial and ventricular stimulation pulses; a set of sensing circuits comprised of sense amplifiers for sensing and amplifying the cardiac signals; a data acquisition system, such as an A/D converter for sampling and acquiring cardiac signals; and pulse generators for generating atrial and ventricular stimulation pulses. In addition, the stimulation device includes memory for storing operational parameters for the control system, such as stimulation parameter settings and sensing parameter settings. The device also includes a telemetry circuit for communicating with an external programmer.

When operating according to a preferred embodiment, recharge and block overlap signals are applied to the sensing circuitry such that recharge and block overlap intervals begin shortly after a delivered stimulation pulse. The block overlap interval extends slightly longer than the recharge interval and ends at a time approximately equal to the time of the most negative point of the evoked response, prior to its positive peak. This application of recharge and block overlap intervals results in an evoked response signal with a primarily positive polarity and a polarization signal with a primarily negative polarity.

A capture detection window is set to begin after the recharge and block overlap intervals expire. During the capture detection window, a post-stimulation signal is acquired. The polarity of a post-stimulation signal feature, such as the peak amplitude or the signal integral, is determined. Detection of a positive polarity of the chosen signal feature confirms capture whereas detection of a negative polarity confirms loss of capture.

The methods and features included in the present invention improve capture detection by sensing an evoked response using methods that minimize interference by the polarization signal artifact allowing improved discrimination between evoked response and polarization signals.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout. The present invention is directed at providing automatic capture verification in an implantable cardiac stimulating device possessing pacemaking, cardioversion and defibrillation capabilities. A general cardiac stimulation device will thus be described in conjunction with FIGS. 1 and 2, in which the capture detection circuitry and methods included in the present invention could be implemented. It is recognized, however, that numerous variations of such a device exist in which the methods of the present invention could be implemented without deviating from the scope of the present invention.

Figure 1:
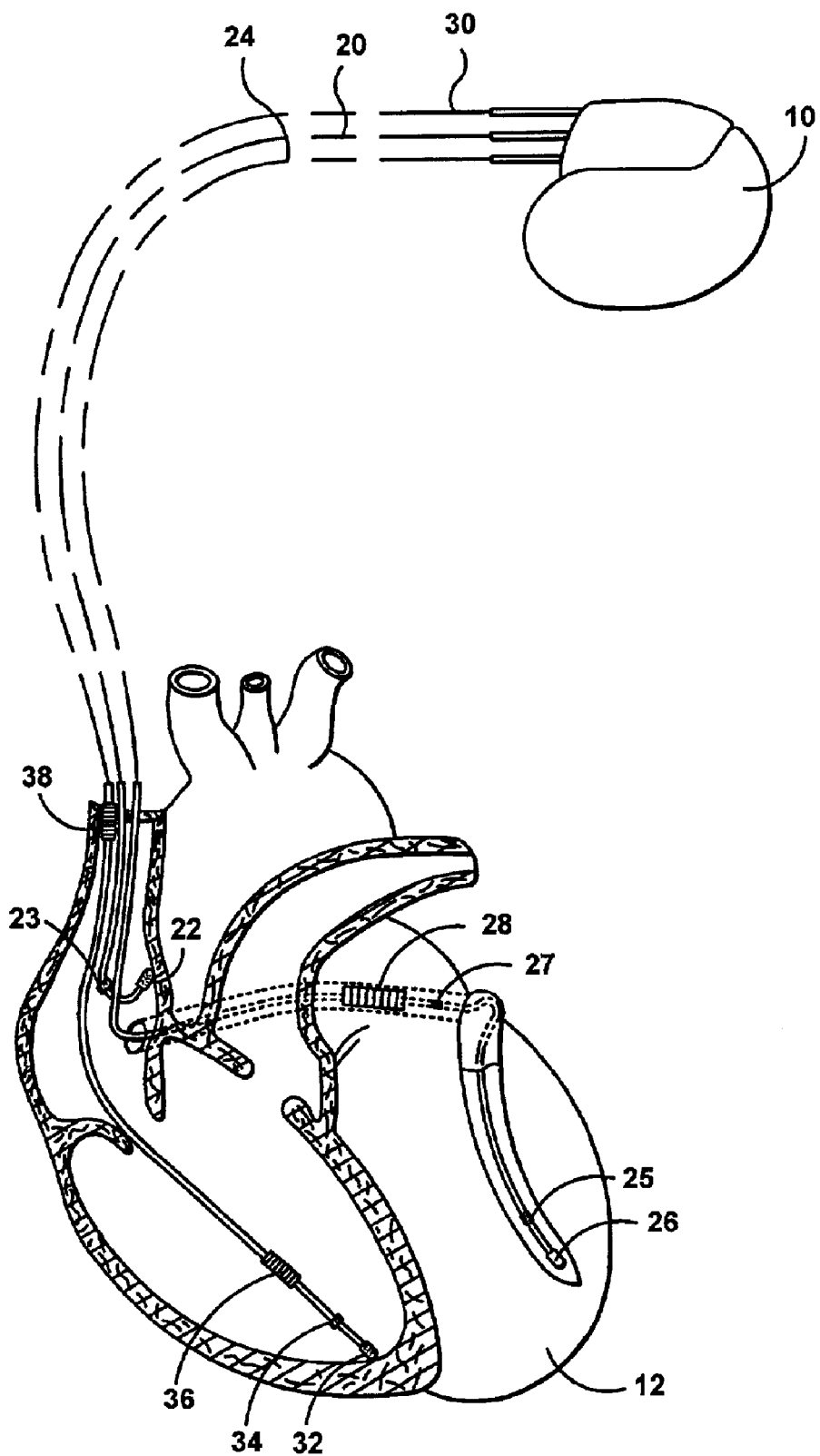
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using: at least a left ventricular tip electrode 26 for unipolar configurations or in combination with left ventricular ring electrode 25 for bipolar configurations; left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
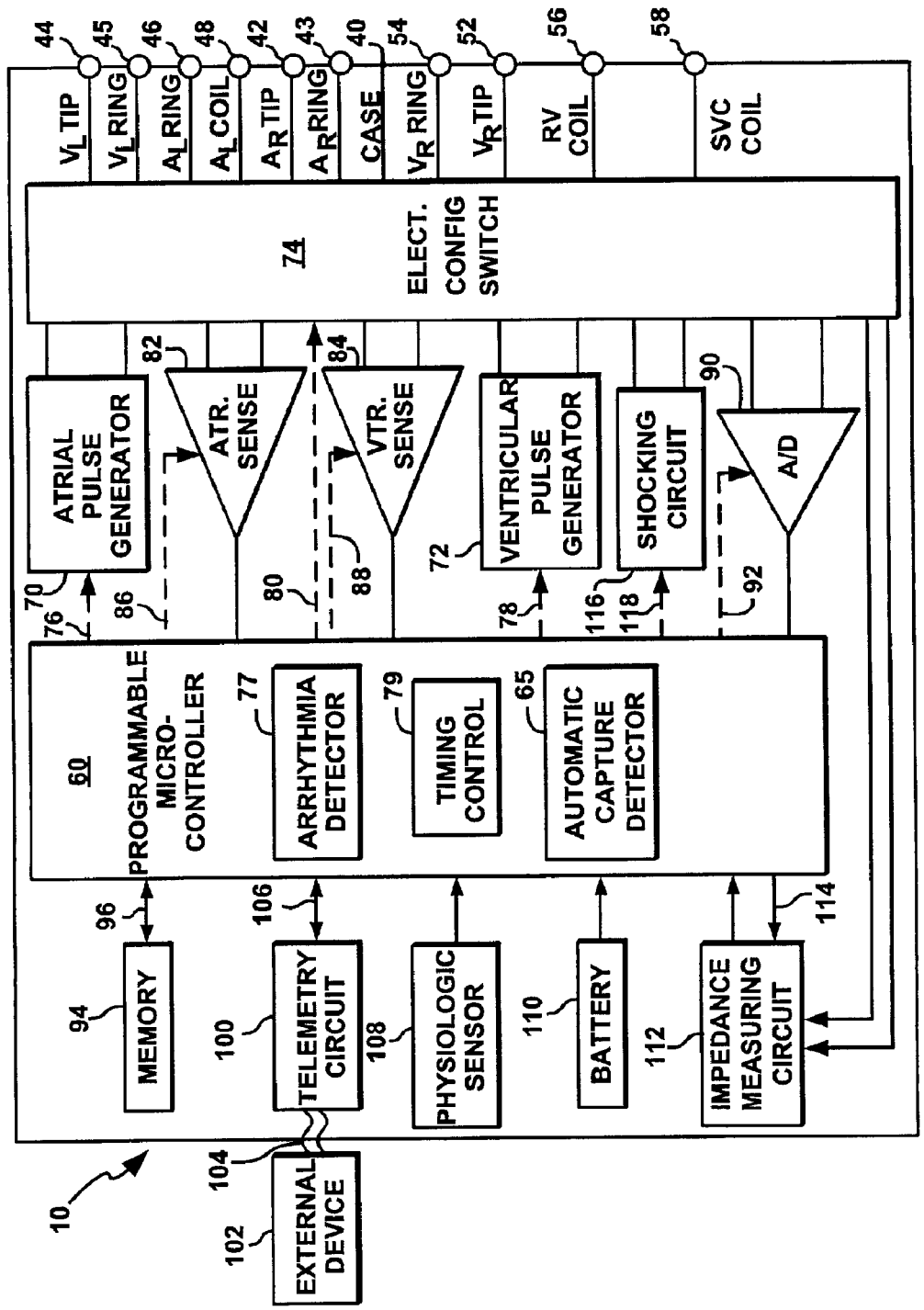
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal (V$_R$ TIP) 52, a right ventricular ring terminal (V$_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. A suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

As it will be described in conjunction with FIGS. 3 through 5, a recharge timing signal and a block overlap timing signal will be applied to corresponding recharge and block overlap circuitry included in a capture detection circuit that may use atrial sensing circuit 82 or ventricular sensing circuit 84 for detecting an evoked response.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during a "detection window" set by timing control circuitry 79 within microcontroller 60.

The microcontroller 60 enables the data acquisition system 90 via control signal 92 to sample the cardiac signal that falls in the evoked response detection window, also referred to herein as the "capture detection window." In accordance with one embodiment of the present invention, the sampled signal is evaluated to determine if it is an evoked response signal based on the polarity of a signal feature such as amplitude, integral, or another signal feature or combination of features. The detection of an evoked response during the evoked response detection window indicates that capture has occurred. Capture detection may occur on a beat-by-beat basis or on a sampled basis. When loss of capture is detected, a safety, back-up pulse is delivered shortly after the primary pulse in order to prevent asystole. Preferably, a capture threshold search is then performed in order to re-determine the threshold and appropriately adjust the stimulation pulse output.

A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, interventricular or interatrial delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 µA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
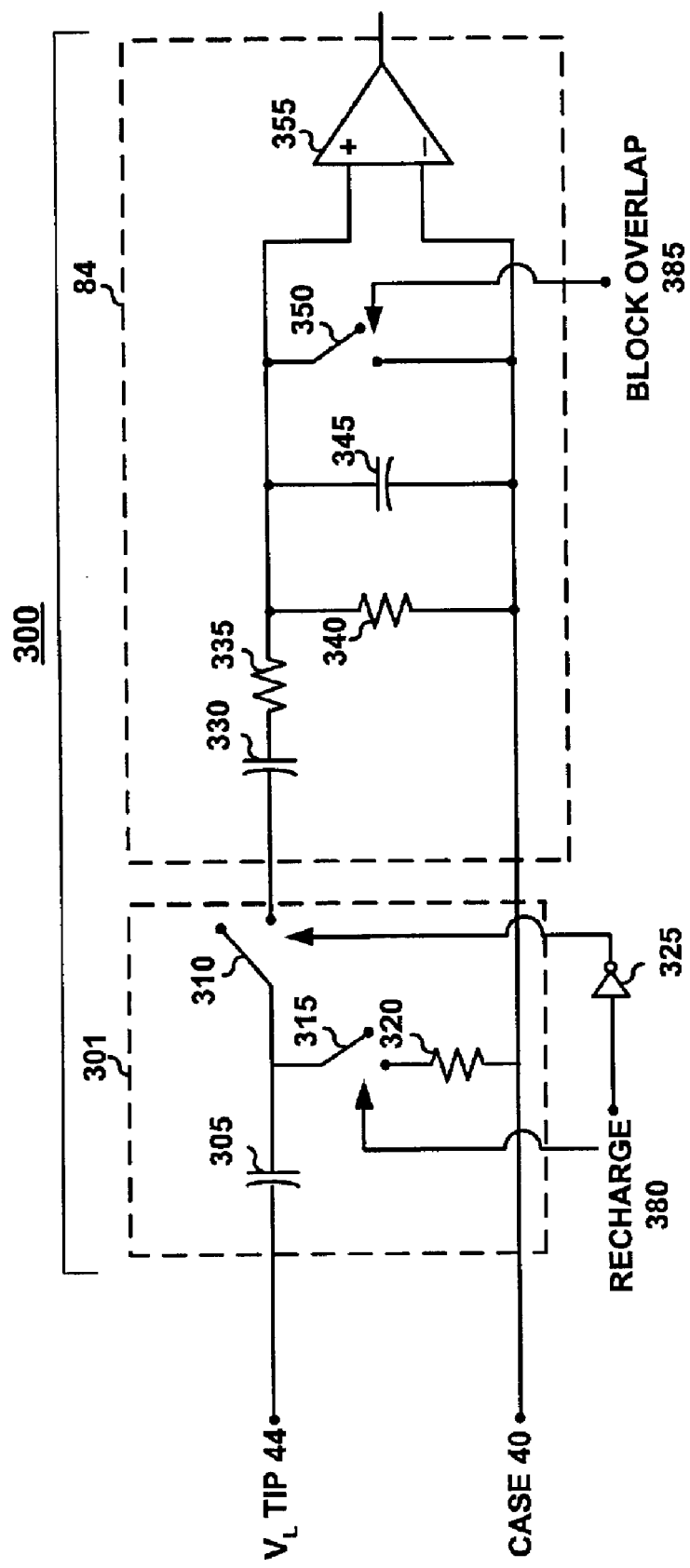
FIG. 3 is a diagram illustrating a capture detection circuit included in one embodiment of the device of FIGS. 1 and 2 for sensing a post-stimulation cardiac signal, for the purpose of verifying capture.

In FIG. 3, a diagram is shown depicting a capture detection circuit 300 implemented in one embodiment of the device 10 to allow automatic capture verification in accordance with the present invention. In this example, the capture detection circuit 300 is shown to include ventricular sensing circuit 84 and to be connected to the left ventricular tip electrode terminal 44 and the case electrode terminal 40. However, the elements of the capture detection circuit 300 could readily be applied to any desired sensing electrodes and designated sense amplifier such that atrial, ventricular or cross-chamber intracardiac electrogram signals may be sensed for the purposes of capture verification. Capture detection circuit 300 may therefore be used to detect an evoked response using unipolar or bipolar sensing configurations.

In the embodiment shown in FIG. 3, the ventricular sensing circuit 84 is coupled to the sensing electrode terminal 44 by an input capacitor 305, and a switch 310. A switch 315, in series with a resistor 320, is connected in parallel to the ventricular sensing circuit 84. The resistor 320 is a low level resistor, preferably 50 ohms. The switch 315, the resistor 320, the capacitor 305, and the switch 310 provide the "recharge circuitry" 301 of the capture detection circuit 300.

The ventricular sensing circuit 84 includes a sense amplifier 355. The positive input node of the sense amplifier 355 is connected to the left ventricular tip terminal 44 via the recharge circuitry 301 and a capacitor 330, preferably a 33 nanofarad capacitor, connected in series with a resistor 335, preferably a 40 kilo ohm resistor. The negative input node of the sense amplifier 355 is connected to the case electrode 40. A resistor 340, a capacitor 345, and a switch 350 are connected in parallel between the positive input node of the sense amplifier 355 and the ground node, provided by the case electrode 40. The resistor 340 is large, preferably 20 megaohms. The capacitor 345 is small, preferably 40 picofarads.

In operation, a recharge signal 380 is applied to the switch 315. The recharge signal 380 is also applied to the switch 310 after first being inverted through an inverter 325. A block overlap signal 385 is applied to the switch 350. The timing of the recharge signal 380 and block overlap signal 385 is illustrated in FIG. 4. Following a ventricular pacing pulse 375, the recharge signal 380 and the block overlap signal 385 are enabled. The recharge signal 380 closes switch 315 connecting the low impedance resistor 320 across the sensing electrode terminals 44 and 40. This removes much of the afterpotential on the Hemholtz capacitance between the sensing electrodes thereby reducing the effect of lead polarization on evoked response sensing. The inverted recharge signal opens the switch 310, decoupling the ventricular sensing circuit 84 from the recharge circuitry 301 during this time immediately following the pacing pulse 375 in which the lead polarization signal is varying. The capture detection circuit 300 may include additional blanking circuitry for absolute blanking of the capture detection circuit 300 during the stimulation pulse delivery.

The block overlap signal 385 remains enabled for a time, on the order of milliseconds, after the recharge signal 380 is disabled. When the recharge signal 380 is disabled, the switch 315 is opened, and the switch 310 is closed reconnecting the ventricular sensing circuit 84 to the sensing electrode terminals 44 and 40. The switch 350 remains closed as long as the block overlap signal 385 is enabled, maintaining a short circuit across the amplifier 355 input, and shorting out the capacitor 345 and resistor 340. During this time, the evoked response signal is varying while the lead polarization signal is decaying.

Figure 5:
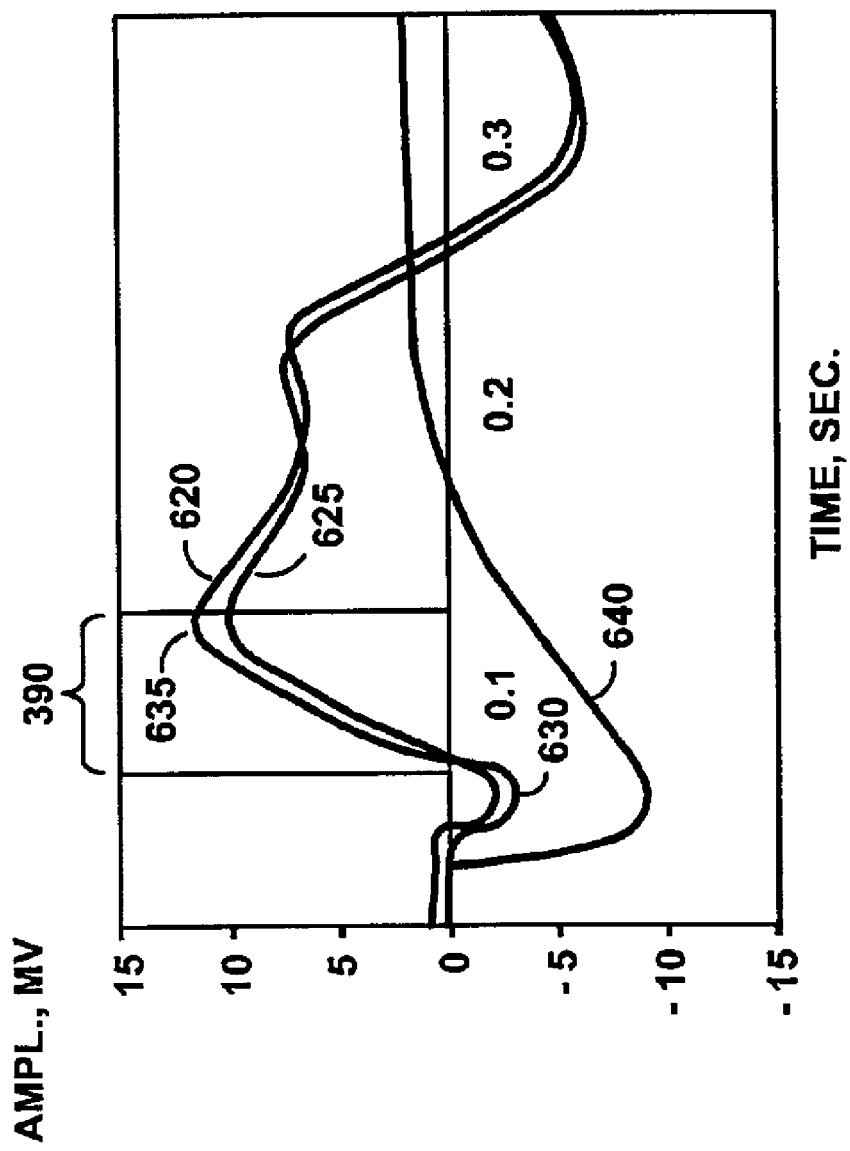
FIG. 5 is a graphical depiction of sample evoked response signals and a polarization signal that could be detected using the circuit of FIG. 3.

An evoked response signal and a lead polarization signal are illustrated in the graph shown in FIG. 5. The intracardiac electrogram signal amplitude, in mV, is plotted along the vertical axis. Time, in seconds, is plotted along the horizontal axis. The polarization signal 640 is seen to be a primarily negative going signal, reaching a negative peak within 0.1 seconds after a stimulation pulse delivered at 0 seconds. The signals 620 and 625 represent the evoked response signal following a stimulation pulse delivered at 4.5 V and 2.5 V amplitude, respectively. The evoked response signal will be consistent in morphology over a range of pulse amplitudes that exceed the capture threshold. As the polarization signal 640 begins to decay back to 0 mV, the evoked response signals 620 and 625 are seen to rise from a negative peak 630 to a positive peak 635. The methods included in the present invention are based on the assumption that in practice the lead polarization signal and the evoked response signal will be of substantially opposite polarity when detected using the capture detection circuit 300.

Figure 4:
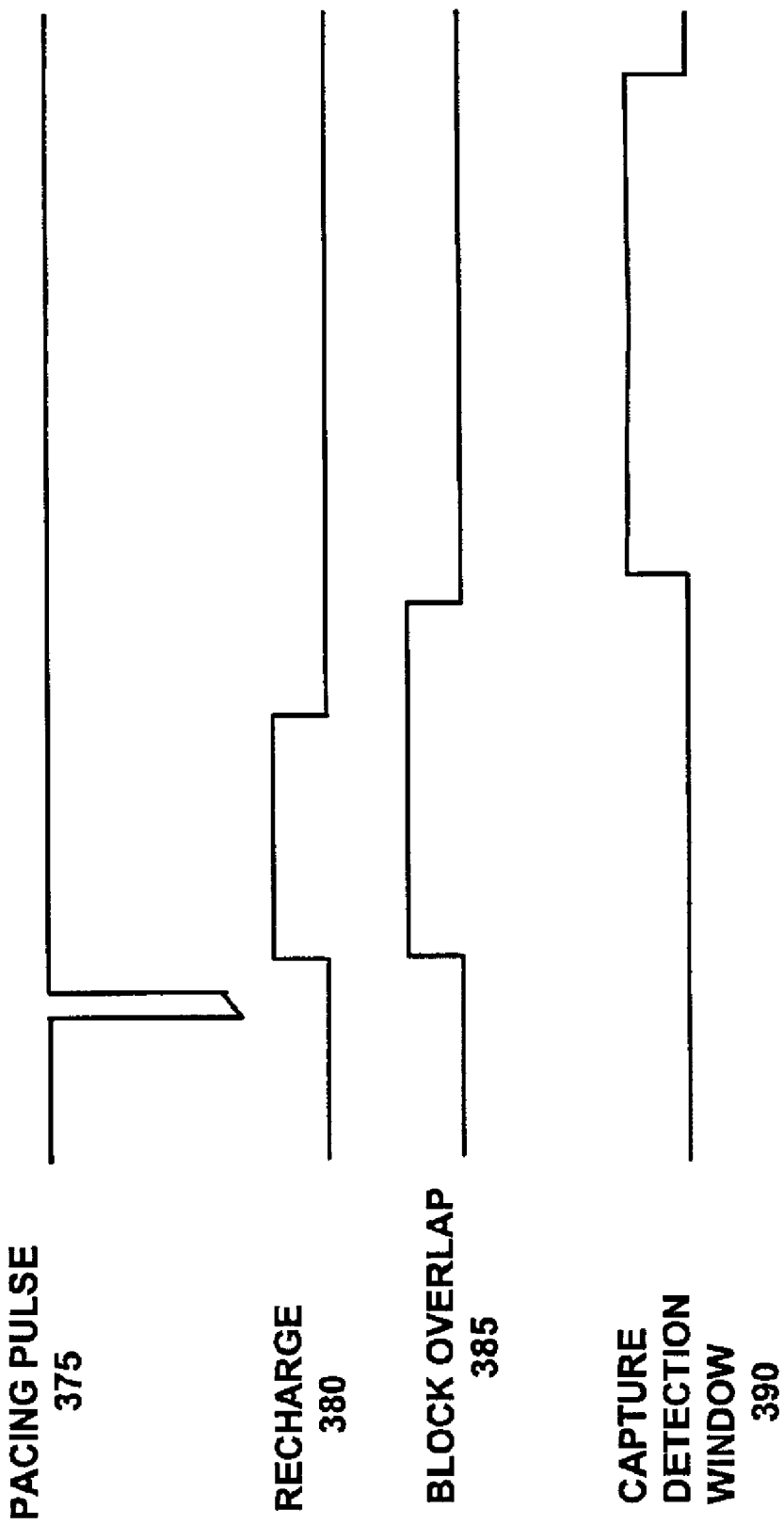
FIG. 4 is a timing diagram illustrating the approximate temporal relationships between a delivered stimulation pulse, a recharge signal, a block overlap signal, and a capture detection window, used by the circuitry of FIG. 3.

When the block overlap signal 385 shown in FIG. 4 is disabled, the switch 350 shown in FIG. 3 opens. The capacitor 345 holds the voltage potential at 0 mV at the start of tracking the evoked response signal by the amplifier 355. The large impedance resistor 340 acts as a voltage divider assuming a voltage potential approximately equal to the evoked response, typically on the order of ninety-nine percent of the evoked response potential. In operation, the block overlap signal 385 is preferably disabled at the negative peak 630 (FIG. 5) of the evoked response signal. A capture detection window 390, shown in FIGS. 4 and 5, is enabled after the block overlap signal 385 is disabled. Thus, by appropriately setting the recharge and block overlap intervals, the capture detection circuit 300 will allow discrimination of the evoked response from the polarization signal by determining the polarity, positive or negative, of a feature of the intracardiac electrogram signal sensed during the capture detection window 390.

Figure 6:
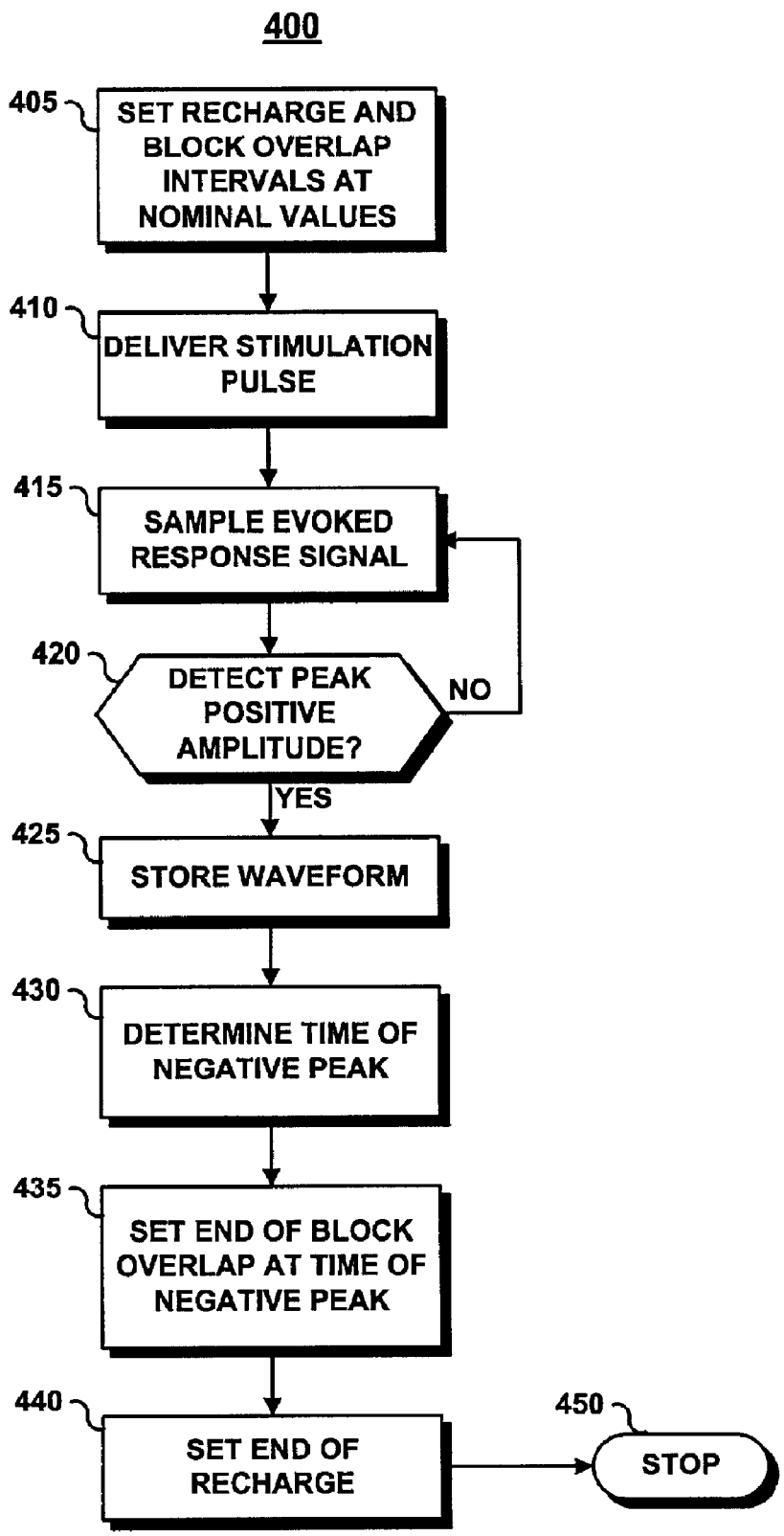
FIG. 6 is a flow chart illustrating the operation of one embodiment of the present invention for determining the appropriate recharge and block overlap interval settings to be applied to the circuit of FIG. 3.

In FIG. 6, a flow chart is shown describing an overview of the operation and novel features implemented in one embodiment of the device 10 for setting the recharge and block overlap intervals appropriately for capture detection. The recharge and block overlap intervals refer to the period of time that the recharge and block overlap signals 380 and 385 are enabled. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

At step 405, the method 400 begins by setting the recharge and block overlap intervals to nominal values. At step 410, a stimulation pacing pulse is delivered to the heart 12 at an energy known to cause capture, for example 4.5 V, using a desired stimulation electrode pair. At step 415, the post-stimulation evoked response signal sensed by the capture detection circuit 300 is sampled by the data acquisition system 90 until a peak positive amplitude 635 is detected by the automatic capture detector 65 at decision step 420. At step 425, the sampled evoked response waveform is stored in memory 94 so that it may be analyzed at step 430 to determine the time of the evoked response negative peak 630. The block overlap signal 385 is set to be disabled at the time of the evoked response negative peak 630 at step 435. At step 440, the recharge interval is set such that the recharge signal 380 is disabled a predetermined number of milliseconds prior to disabling the block overlap signal 385. At step 450, the method 400 is terminated having set the recharge and block overlap intervals appropriately for capture detection.

The method 400 is preferably executed whenever automatic capture verification is initially enabled. The method 400 may be repeated periodically so that the recharge and block overlap intervals may be adjusted as necessary if changes in the evoked response signal occur over time.

Figure 7:
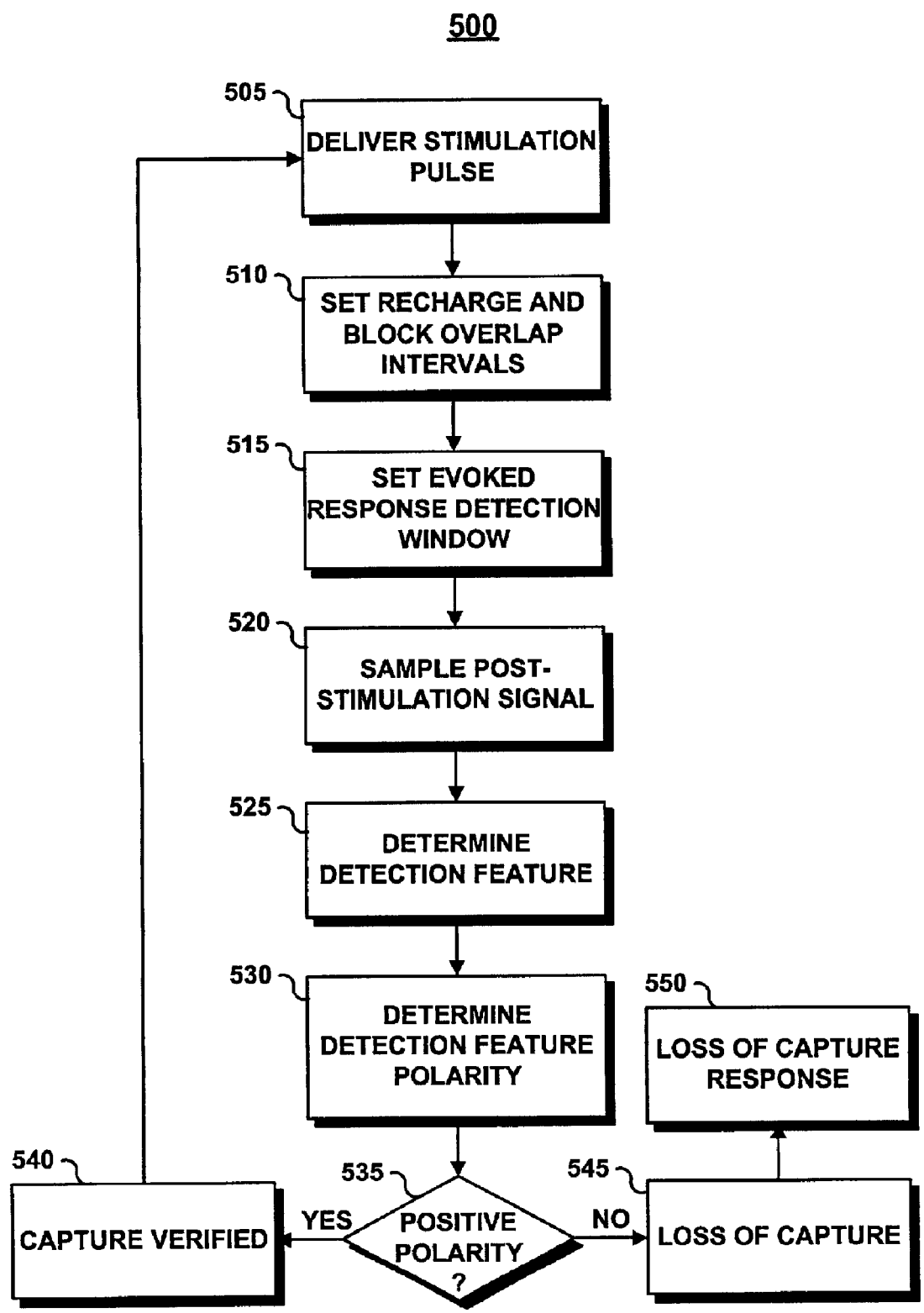
FIG. 7 is a flow chart illustrating the operation included in one embodiment of the present invention for performing capture verification by determining the polarity of a signal detection feature derived from a post-stimulation signal sensed by the circuit of FIG. 3.

Once the recharge and block overlap intervals have been appropriately set, automatic capture may be enabled. The flow chart shown in FIG. 7 provides an overview of the operation of the automatic capture feature included in one embodiment of the present invention. The method 500 shown in FIG. 7 is executed by automatic capture detector 65 to determine the polarity of a post-stimulation signal feature upon which capture verification is based. The signal feature used to detect capture may be, for example, a peak signal amplitude or a signal integral found during the capture detection window 390.

At step 505, the method 500 begins when a stimulation pulse is delivered from either atrial pulse generator 70 or ventricular pulse generator 72 to the desired atrial or ventricular heart chamber during normal device 10 operation. At step 510, the recharge and block overlap signals 380 and 385 are enabled according to the intervals determined by the method 400. At step 515, the capture detection window 390 is enabled. This window begins shortly after the block overlap signal 385 is disabled and extends for a predetermined period of time during which an evoked response is expected to occur, typically within 150 ms of the stimulation pulse. At step 520, the post-stimulation intracardiac electrogram signal is sampled by the capture detection sensing circuit 300 during the capture detection window 390 using the designated sensing electrodes for capture detection.

At step 525, a detection feature of the sampled signal is determined. The detection feature may be a peak amplitude, integral or any other predetermined feature of the post-stimulation signal that may be used to determine the characteristic polarity of the signal, either positive or negative, thereby allowing distinction between capture and loss of capture. If the signal feature for detecting capture is a signal integral, the capture detection window 390 defines an integration interval during which all signal samples are integrated to determine the detection feature value.

Figure 8:
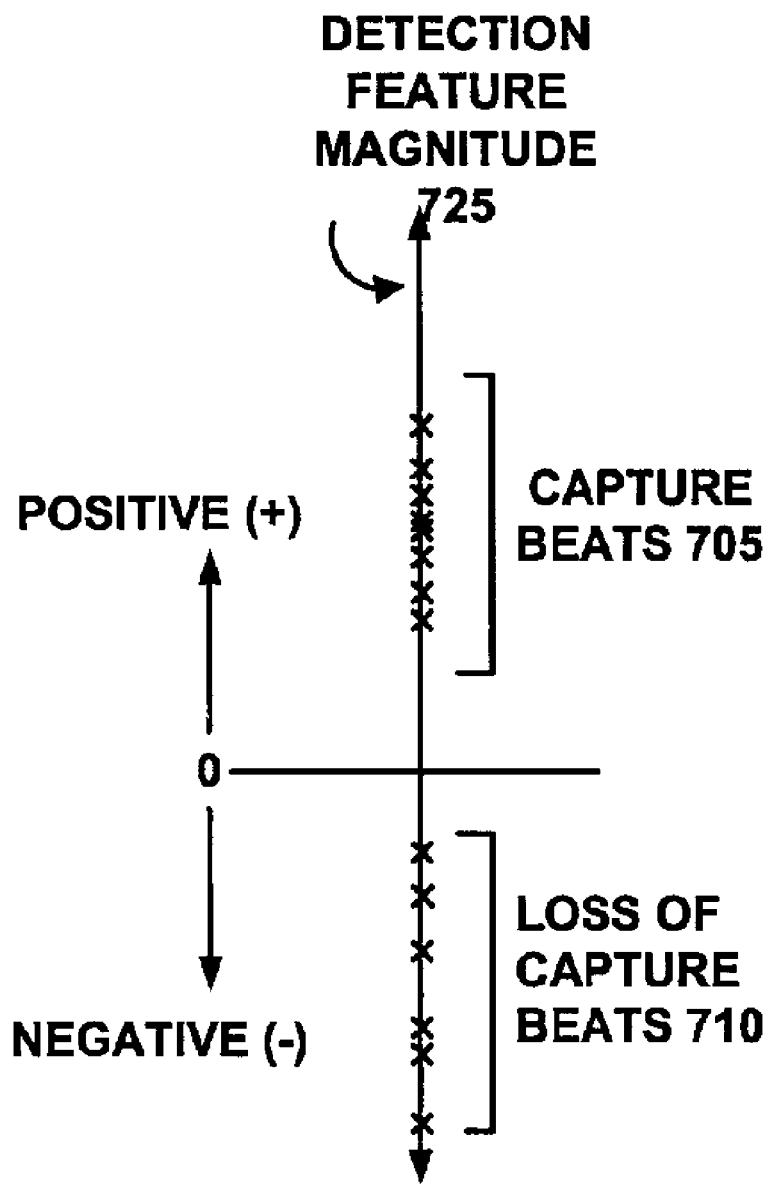
FIG. 8 is a plot illustrating sample results of the operations of FIG. 7 in which the polarity of a signal detection feature is determined in order to identify captured beats and non-captured beats.

At step 530, the polarity of the detection feature value is determined. An example of a polarity map 700 is shown in FIG. 8. The magnitude of the detection feature is mapped along an axis 725. A number of hypothetical points are plotted having a positive polarity, representing detection feature values for captured beats 705. Likewise, a number of hypothetical points are plotted having a negative polarity, representing detection feature values for loss of capture beats 710. Hence, if the detection feature is found to have a positive polarity at decision step 535 of FIG. 7, capture is verified at step 540. The capture detection method 500 returns to step 505 to await the next stimulation pulse. If the detection feature is found to have a negative polarity, loss of capture is detected at step 545. A loss of capture response may then be invoked by device 10 at step 550, which typically includes delivery of a safety backup stimulation pulse and may include a threshold search if the loss of capture is sustained for more than one cardiac cycle.

In other embodiments, the polarity detection may be performed in conjunction with other capture detection criteria related to the detection feature magnitude, such as a minimum peak amplitude or minimum integral value, before verifying capture.

In an alternative embodiment, a capture detection method for determining a signal feature may process signal samples that are only positive or only negative in polarity. For example, if the detection feature is a signal integral, only positive signal samples during the capture detection window are integrated. If integration of the positive signal samples results in an integral value meeting a capture detection criteria, capture is verified. If no positive signal samples are found for integration, then loss of capture is detected.

The problem of lead polarization normally encountered in detecting an evoked response is overcome by incorporating the techniques provided by the present invention. These techniques advantageously prevent the polarization artifact from interfering with evoked response detection, without dramatically affecting the evoked response signal and thus allowing reliable capture detection.

Thus, a system and method for reliably detecting capture without requiring complex signal processing algorithms or additional sensors has been described. Using the methods provided herein, interference of the polarization signal in verifying capture is minimized. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of automatically verifying capture for use in a cardiac stimulation device, the method comprising:
   delivering a stimulation pulse;
   setting a capture detection window;
   detecting a post-stimulation cardiac signal sensed during the capture detection window;
   identifying a polarity of an amplitude of the post-stimulation cardiac signal;
   confirming capture if the amplitude has a predetermined polarity; and
   confirming loss of capture if the amplitude has a different polarity than the predetermined polarity.

2. The method of claim 1, further comprising coupling an intracardiac electrogram sensing circuit to a sensing electrode via a recharge circuit and a block overlap circuit.

3. The method of claim 2, further comprising setting a recharge interval and a block overlap interval to begin after the delivery of a stimulation pulse; and
   enabling a recharge signal and a block overlap signal during the recharge interval and the block overlap interval.

4. The method of claim 3, further comprising applying a recharge signal to the recharge circuit during the recharge interval so that the intracardiac electrogram sensing circuit is temporarily uncoupled from a sensing electrode, and an electrode polarization afterpotential is reduced across a load.

5. The method of claim 4, further comprising setting a block overlap interval to expire at approximately the same time that a negative peak of an evoked response signal occurs.

6. The method of claim 5, wherein a duration of the block overlap interval exceeds the recharge interval by a predetermined amount of time.

7. The method of claim 6, further comprising enabling a block overlap signal to be applied to the block overlap circuitry during the block overlap interval.

8. The method of claim 7, further comprising disabling the block overlap signal upon the expiration of the block overlap interval, is disabled.

9. The method of claim 8, wherein setting the capture detection window comprises enabling the capture detection window after disabling the block overlap signal.

10. The method of claim 1, wherein identifying a positive polarity of the amplitude confirms capture and identifying a negative polarity of the amplitude confirms loss of capture.

11. The method of claim 10, wherein identifying the polarity of the amplitude comprises identifying any of a peak amplitude or a signal integral.

12. The method of claim 1, wherein confirming capture comprises comparing a magnitude of the amplitude to a predetermined capture detection criterion.

13. The method of claim 1, further comprising delivering a back-up stimulation pulse if loss of capture is confirmed.

14. The method of claim 1, further comprising performing a threshold test if loss of capture is confirmed.

15. The method of claim 1, wherein sampling the cardiac signal further comprises selecting cardiac signal samples having a predetermined polarity.

16. The method of claim 15, wherein determining the amplitude comprises determining an amplitude only from selected cardiac signal samples having a predetermined polarity.

17. A cardiac stimulation device capable of automatically verifying capture, comprising:
   a pulse generator that selectively generates a stimulation pulse for delivery to one or more cardiac chambers;
   a timing circuit, connected to the pulse generator, that sets a capture detection window;
   a sensor that senses post-stimulation cardiac signals during the detection windows;
   a detector that identifies a polarity of an amplitude of the post-stimulation cardiac signals; and
   a control circuit that confirms capture if the amplitude has a predetermined polarity, and that confirms loss of capture if the amplitude has a different polarity than the predetermined polarity.

18. The stimulation device of claim 17, further comprising a recharge circuit and a block overlap circuit that couple an intracardiac electrogram sensing circuit to a sensing electrode.

19. The stimulation device of claim 18, wherein the timing circuit sets a recharge interval and a block overlap interval to begin after the delivery of a stimulation pulse; and
   wherein the control circuit enables a recharge signal and a block overlap signal during the recharge interval and the block overlap interval.

20. The stimulation device of claim 19, wherein the timing circuit further applies a recharge signal to the recharge circuit during the recharge interval so that the intracardiac electrogram sensing circuit is temporarily uncoupled from a sensing electrode, and an electrode polarization afterpotential is reduced across a load.

21. The stimulation device of claim 20, wherein the timing circuit further sets a block overlap interval to expire at approximately the same time that a negative peak of an evoked response signal occurs.

22. The stimulation device of claim 21, wherein a duration of the block overlap interval exceeds the recharge interval by a predetermined amount of time.

23. The stimulation device of claim 22, further comprising a switch that enables a block overlap signal to be applied to the block overlap circuitry during the block overlap interval.

24. The stimulation device of claim 23, wherein the switch disables the block overlap signal upon the expiration of the block overlap interval.

25. The stimulation device of claim 24, wherein the timing circuit enables the capture detection window after disabling the block overlap signal.

26. The stimulation device of claim 17, wherein the predetermined polarity of the amplitude is any of a positive polarity or a negative polarity.

27. The stimulation device of claim 26, wherein the polarity of the amplitude is any of a peak amplitude or a signal integral.

28. The stimulation device of claim 17, wherein the pulse generator is any of an atrial pulse generator or a ventricular pulse generator.

29. The stimulation device of claim 28, wherein the sensor is any of a ventricular sensing circuit or an atrial sensing circuit.

30. The stimulation device of claim 29, wherein the sample comprises an analog-to-digital converter.

31. A cardiac stimulation device capable of automatically verifying capture, comprising:
   means for selectively delivering a stimulation pulse to one or more cardiac chambers;
   means for sensing a post-stimulation cardiac signal following delivery of a stimulation pulse;
   means for identifying a polarity of an amplitude of the post-stimulation cardiac signals; and
   means for confirming capture if the amplitude has a predetermined polarity, and that confirms loss of capture if the amplitude has a different polarity than the predetermined polarity.

32. The stimulation device of claim 31, further comprising a recharge means and a block overlap means that couple an intracardiac electrogram sensing circuit to a sensing electrode.

33. The stimulation device of claim 32, further comprising means for setting a recharge interval and a block overlap interval to begin after the delivery of a stimulation pulse; and
   wherein the means for confirming enables a recharge signal and a block overlap signal during the recharge interval and the block overlap interval.

34. The stimulation device of claim 33, further comprising means for applying a recharge signal to the recharge means during the recharge interval so that the intracardiac electrogram sensing circuit is temporarily uncoupled from a sensing electrode, and an electrode polarization afterpotential is reduced across a load.

35. The stimulation device of claim 34, further comprising means for setting a block overlap interval to expire at approximately the same time that a negative peak of an evoked response signal occurs; and
   wherein a duration of the block overlap interval exceeds the recharge interval by a predetermined amount of time.

36. The stimulation device of claim 35, further comprising a switch that enables a block overlap signal to be applied to the block overlap means during the block overlap interval, and that further disables the block overlap signal upon the expiration of the block overlap interval.

37. The stimulation device of claim 31, wherein the predetermined polarity of the amplitude is any of a positive polarity or a negative polarity.

* * * * *